US012692367B2

(12) United States Patent
Bernard et al.

(10) Patent No.: US 12,692,367 B2
(45) Date of Patent: Jul. 28, 2026

(54) RHEOLOGY ADDITIVES BASED ON DI- OR TRI-AMIDES AND MIXTURES THEREOF

(71) Applicant: Arkema France, Colombes (FR)

(72) Inventors: Michael Y. Bernard, Enghien-les-Bains (FR); Dmitri Colesnic, Paris (FR); Laurent Lepinay, Meru (FR); Vincent Leroy, Fitz James (FR); Francois Vettier, Chatou (FR)

(73) Assignee: Arkema France, Puteaux (FR)

( * ) Notice: Subject to any disclaimer, the term of this patent is extended or adjusted under 35 U.S.C. 154(b) by 636 days.

(21) Appl. No.: 16/766,019

(22) PCT Filed: Oct. 24, 2018

(86) PCT No.: PCT/FR2018/052643
§ 371 (c)(1),
(2) Date: May 21, 2020

(87) PCT Pub. No.: WO2019/102087
PCT Pub. Date: May 31, 2019

(65) Prior Publication Data
US 2020/0354545 A1      Nov. 12, 2020

(30) Foreign Application Priority Data

Nov. 21, 2017    (FR) ..................................... 1760983

(51) Int. Cl.
| | |
|---|---|
| *A01N 43/00* | (2006.01) |
| *A01N 43/46* | (2006.01) |
| *A61K 31/55* | (2006.01) |
| *C07C 233/05* | (2006.01) |
| *C08K 5/20* | (2006.01) |
| *C09J 177/00* | (2006.01) |

(52) U.S. Cl.
CPC .............. *C08K 5/20* (2013.01); *C07C 233/05* (2013.01); *C09J 177/00* (2013.01)

(58) Field of Classification Search
CPC .. C08K 5/20; C08K 5/101; C08J 3/223; C08J 3/24; C08J 2333/06; C08J 2333/14; C08J 2363/00; C08J 2433/14; C08J 2435/02; C09D 4/06; C09D 7/63; C09D 11/101; C09D 11/102; C09D 11/38; C09D 133/06; C09D 133/14; C09D 7/20; C09D 7/43; C09D 7/80; C09D 163/00; C08F 20/28; C08F 2/44; C08F 2/50
See application file for complete search history.

(56) References Cited

U.S. PATENT DOCUMENTS

| | | | |
|---|---|---|---|
| 5,082,469 A | 1/1992 | Kain et al. | |
| 10,029,978 B2 | 7/2018 | Bernard | |
| 2004/0261656 A1 | 12/2004 | Wu et al. | |
| 2008/0223519 A1* | 9/2008 | Locko .................. | C08G 18/348 |
| | | | 156/331.7 |
| 2008/0235191 A1 | 9/2008 | Dijk et al. | |
| 2015/0094245 A1 | 4/2015 | Gieselman et al. | |
| 2015/0274644 A1 | 10/2015 | Bernard et al. | |
| 2016/0168079 A1 | 6/2016 | Bernard | |
| 2016/0312005 A1 | 10/2016 | Bernard et al. | |

FOREIGN PATENT DOCUMENTS

| | | | |
|---|---|---|---|
| CN | 107099029 A | 8/2017 | |
| JP | S61234919 A | 10/1986 | |
| WO | WO9814493 | 4/1998 | |
| WO | WO-2008080536 A1 * | 7/2008 | ............... A61K 8/42 |

OTHER PUBLICATIONS

"Amines" [online], Tomoe Industries Co. Ltd. (retrieved May 20, 2022) <URL:https://www.tomo-e.co.jp/chemical/products/detail.php?id=25QU050.

* cited by examiner

*Primary Examiner* — Layla Soroush
(74) *Attorney, Agent, or Firm* — Debodhonyaa Sengupta

(57)      ABSTRACT

The invention relates to a fatty amide which is a di- or triamide based on a polyether diamine or triamine which can be used as organogelator and in particular as rheology additive. The invention also relates to a formulation composition using said fatty amide as rheology additive and to its use with this aim in coating, adhesive or PVC plastisol compositions and in particular transparent or non-transparent mastic compositions. said rheology additive has the advantage of not needing a specific activation process before use, in contrast to the other known fatty amide additives based on hydrogenated castor oil derivatives.

18 Claims, No Drawings

RHEOLOGY ADDITIVES BASED ON DI- OR TRI-AMIDES AND MIXTURES THEREOF

CROSS-REFERENCE TO RELATED APPLICATIONS

This application is a national stage application under 35 U.S.C. § 371 of PCT/FR2018/052643, filed Oct. 24, 2018, which claims benefit to application FR 1760983, filed Nov. 21, 2017.

The present invention relates to a specific polyfunctional amide (di- and triamide) suitable for being used as organogelator, in particular as rheology additive and more particularly in coating compositions.

BACKGROUND

EP 1 514 912 describes branched triamides of non-hydroxylated fatty acids based on polyether amines and used as phase-change vector agent in phase-change inks (known as "hot melt inks") with the function of causing the ink to pass from the solid state at ambient temperature to the liquid state at high temperature in inkjet printers and making it possible for the liquid ink droplets to solidify rapidly after they have been squirted at this temperature. EP 1 514 912 does not in the least suggest the use of these polyamides as organogelator agent or thixotropic agent and does not in the least suggest polyamides carrying non-terminal hydroxy by the fatty acid used.

Fatty diamides based on aliphatic diamines (without polyether segments) and based on hydroxylated fatty acids are known as organogelator agents and in particular as thixotropic agents.

WO 2014/053774 describes hydroxylated fatty acid diamides as organogelator agent or also known as rheology additive, in particular in coating, moulding, mastic or leaktightness agent or cosmetic compositions.

WO 2015/011375 describes fatty acid diamines comprising, in their structure, both cycloaliphatic and aliphatic diamines with a specific molar ratio and the use of these products as organogelator agent or as rheology additive, in particular in coating, moulding, mastic or leaktightness agent or cosmetic compositions.

FR 2 993 885 describes a fatty acid diamide comprising, in its structure, specific hydroxylated carboxylic acids and the use of this product as organogelator in coating, moulding, mastic or leaktightness agent compositions.

Diamides of this type need to be micronized in the powder state and subsequently need an "activation" beforehand in order to give the required rheological performance qualities. The activation process requires a high-speed shearing and a heating sometimes ranging up to 100° C., depending on the products. Furthermore, a minimum period of time is required, which depends on the temperature conditions and on the polarity of the system. Moreover, these additives may not be very compatible with some binders for reactive formulations or with some diluents or plasticizers used for the activation. Consequently, this activation phase constitutes a particular disadvantage for polyamide powders and hydrogenated castor oil derivatives used as additives in this field.

There is thus a need for novel fatty polyamides which make possible simpler and easier shaping and use (shaped in the form of flakes readily soluble in the plasticizers or binders of final application reactive formulations, without the need for preactivation beforehand) with a broader spectrum of compatibility with the reactive binders and plasticizers/diluents used in reactive formulations, such as: silane-terminated polyether, silane-terminated polyurethane, polyurethane terminated by isocyanate, silicone, polysulfide, epoxy, and the like, and resulting in final products having an improved surface and aesthetic appearance, in particular with, in the end, coatings, mastic seals or sealing agent seals which are transparent without surface defect, this being related to the specific structure and specific composition of these targeted polyamides.

DETAILED DESCRIPTION OF THE INVENTION

The present invention, with novel fatty polyamides (polyfunctional fatty amides, in particular di- and triamides) based on primary polyamines (di- and triamines) comprising at least one polyether segment in its structure and in particular based on polyoxypropylene and based on fatty acids comprising at least one hydroxylated fatty acid, makes it possible to meet the new requirements defined above.

The first subject-matter of the present invention relates to a polyfunctional fatty amide which is a fatty diamide or triamide or their mixture, based on a polyether polyamine (diamine or triamine) and on at least one saturated linear fatty acid, at least one of said saturated linear fatty acids of which carries a non-terminal hydroxyl group, and optionally in the presence of another shorter $C_2$-$C_{10}$ acid.

The second subject-matter of the invention relates to a formulation composition of an organic binder, which composition comprises at least one organic binder and at least one fatty amide as defined according to the present invention, in particular as rheological additive.

The present invention also covers the use of at least one fatty amide as defined according to the present invention as rheology additive.

Finally, the invention also covers the final product obtained, which results from the use of at least one fatty amide as defined according to the present invention, as rheology additive, in particular as thixotropic agent.

Thus, the first subject-matter of the present invention is a polyfunctional fatty amide, which is a diamide or a triamide or their mixture, said fatty amide being represented by:

A) according to the following formula (I):

$$R[(—X—R1\text{-}NHCO—R2)n\text{-}n_1][(—X—R1\text{-}NHCO—R2')n_1] \quad (I)$$

with n being 2 or 3, preferably 3, $n_1$ being equal to 0 or 1, —R—(X—R1—)n being the residue of valency n of a primary polyamine R(—X—R1-NH2)n which is a primary diamine or triamine, with each primary amine group —NH2 being a terminal group carried by a bivalent oligomer chain segment R1 chosen from polyether and polyester which is alkoxylated (alkoxylated polyester), preferably polyether and more preferably polyoxypropylene or oxypropylene/oxyethylene copolymers having a predominance of oxypropylene units, R: $C_3$-$C_{10}$ alkylene residue of valency n resulting from a polyol R(OH)n or from a polyamine R(NH2)n or R(NH—R3)n, preferably from a polyol R(OH)n, X: O or N, preferably O, R2 being the $C_{12}$-$C_{52}$, preferably $C_{16}$-$C_{36}$, more preferably $C_{16}$-$C_{24}$, fatty residue of fatty acid R2CO2H, in particular saturated and linear, R2' being the $C_2$ to $C_{10}$, preferably $C_3$ to $C_8$, monocarboxylic acid residue, with at least one R2 residue, preferably at least two, more preferably all the R2 residues, being residue(s) of hydroxylated fatty acid R2CO2H with a non-terminal hydroxyl group and it being possible for said R2 residues to be identical or different, R3 being a $C_1$-$C_2$ alkyl substituent, or (said fatty amide being represented) by:

B) according to the following formula (II), in the case in which said amide is a diamide:

$$R2CONH—R'—O—[CH2—CH(R4)—O]_x—CH2—$$
$$CH(R4)—NHCOR'2 \qquad (II)$$

with R' being the monopropylene glycol residue without OH: —CH(CH3)—CH2—

R2 and R'2 being defined as in formula (I) above, and R4 being H or methyl with the repeat oxyalkylene unit —CH2—CH(R4)—O— being ethoxy when R4 is H and propoxy when R4 is methyl, or R4 corresponds to an ethoxy/propoxy mixture and preferably R4 is methyl with said oxyalkylene unit being propoxy, and said amide having a melting point, meaning melting temperature, measured by DSC after two passes, 10° C./min, ranging from 10 to 110° C., preferably from 25 to 100° C.

The term "melting point" corresponds to the melting temperature measured by DSC at a rate of heating of 10° C./min. This temperature is the temperature which corresponds to the melting peak recorded by DSC at the specified rate of heating.

Regarding the residue R, said $C_3$-$C_{10}$ alkylene, in addition to the carbon-carbon bonds, may comprise an ether bridge —O— in the case of a polyol residue or an —NH— bridge in the case of a polyamine residue.

In the case in which X=N, as appears clearly from the formulae specified above for polyamines containing R residue, this means that N represents —NH— and —N(R3)—.

Regarding the meaning of R2CO2H, this relates to linear hydroxylated fatty acids with non-terminal hydroxy. These linear fatty acids contain a linear $C_{12}$-$C_{52}$, preferably $C_{16}$-$C_{36}$, more preferentially $C_{16}$-$C_{24}$ fatty chain, in particular exclusively consisting of C—C bonds and therefore do not contain ester groups within this linear chain. This definition therefore excludes from the definition of R2CO2H any polyester or oligoester derived from the self-polycondensation of a hydroxylated fatty acid.

Mention may be made, as suitable examples of primary polyamines corresponding to the formula R(—X—R1-NH2)n which are primary diamines or triamines as defined above, of the following:

as amine (n=2) or triamine (n=3): a primary diamine with the two primary amine functional groups carried by a polyether segment or an alkoxylated polyester (polyester-polyether) segment or a triamine with 3 primary amine functional groups carried by 3 polyether or alkoxylated polyester (polyester-polyether) segments, said polyether or alkoxylated polyester segment for a diamine or the combination of the 3 polyether or alkoxylated polyester segments in the case of a triamine having a number-average molecular weight Mn ranging from 500 to 3000. In particular, they are primary diamine and triamine polyethers and more particularly primary diamine and triamine polyoxypropylenes, such as the Jeffamine® diamines and triamines sold by Huntsman with as more specific suitable examples Jeffamine® D-2000 (primary diamine with a polyoxypropylene segment carrying 2 primary amine groups with a number of oxypropylene units of 33) or Jeffamine® T-3000 (primary triamine with 3 polyoxypropylene segments and a total number of oxypropylene units of 50). Other amines can also be used: Jeffamine® D-400, Jeffamine® D-2010, Jeffamine® T-403, Jeffamine® T-5000, and the like.

In principle, said polyether diamines or polyether triamines suitable for preparing the diamides and triamides according to the present invention may be obtained from corresponding polyether polyol (respectively diol or triol) precursors by reductive amination of the terminal OH functions in the presence of a catalyst, as described in U.S. Pat. No. 4,766,245 or GB2175910.

Regarding the respective polyether polyol (diol or triol) precursors of polyether diamines or triamines, they may be obtained by anionic polymerization in basic medium of the corresponding alkylene oxide (ethylene oxide for polyoxyethylene diol/triol, propylene oxide for polyoxypropylene diol/triol) or a mixture of said alkylene oxides in the presence of a polyol alkoxide initiator with primary OH groups, which is respectively diol or triol (with primary OH groups), or a polyamine initiator, respectively diamine and triamine (according to the functionality of said polyether: diol or triol). As example of diol initiator, mention may be made of ethylene glycol, diethylene glycol, 1,3-propylene glycol, 1,4-butylene glycol. As example of triol initiator, mention may be made of trimethylolpropane.

In the case of bivalent initiators (two primary alkoxide functions or two amine functions), they lead to a symmetrical structure with the initiator incorporated in the middle of the chain (via ether bond —O— or —NH— bond) and with the start of a polyether chain for each alkoxide or amine function of the initiator used.

In the case of a trivalent initiator (primary alkoxide triol or triamine), each alkoxide or amine is the starting point for a polyether chain, with the result being 3 polyether chains borne by a molecule of said initiator, the residue of which corresponds to R in the formula defined above for the amide according to the invention.

In the particular case of polyether diamines, the polyether diol precursors may also be obtained by anionic polymerization of the alkylene oxide or of a corresponding mixture of alkylene oxides (for example ethylene oxide or propylene oxide or a mixture of ethylene oxide and propylene oxide for, respectively, polyoxyethylene diols, polyoxypropylene diols and (oxyethylene-oxypropylene) diol copolymers) from a monovalent primary alkoxide initiator bearing an OH on a secondary carbon of said initiator (which secondary OH does not react to open the alkylene oxide). In such a case, a single polyether chain is formed from the primary alkoxide, the other (secondary) OH portion of the initiator remaining free and unchanged and thus, with the polyether formed, being a diol (polyether diamine precursor by conversion of the terminal OHs to NH2 as mentioned above). An example of monovalent diol initiator (1 single primary OH) is monopropylene glycol in the primary alkoxide form, as below:

$$HO—CH(CH3)—CH2O^-$$

In the more particular case of polyether diamines based on polyoxypropylene, the monopropylene glycol acts as monovalent initiator, with secondary hydroxyl being unaffected during the polymerization of the propylene oxide (ring-opening initiation by attack of the anionic alkoxide initiator on the least electron-rich carbon atom (—CH2—) of the propylene oxide and subsequent chain propagation), leading to the polyoxypropylene diol of following formula, which bears two secondary OHs:

$$HO—CH(CH3)—CH2—O—(CH2—CH(CH3)$$
$$—O)_x—CH2—CH(CH3)—OH$$

After conversion of the terminal secondary hydroxyls (by catalyzed reductive amination under NH3 pressure as described in U.S. Pat. No. 4,766,245 or GB2175910), the polyoxypropylenediamine of following formula may be obtained:

$$H_2N—CH(CH_3)—CH_2O—(CH_2—CH(CH_3)—O)_x—CH_2—CH(CH_3)—NH_2$$

As example of such a polyoxypropylenediamine, mention may be made of Jeffamine® D2000, sold by Huntsman.

Use may be made, as hydroxylated saturated linear fatty acids $R_2CO_2H$ (with $R_2$ carrying a non-terminal OH) as defined according to the invention, of a hydroxy fatty acid chosen from 12-hydroxystearic acid (12-HSA), 9-hydroxystearic acid (9-HSA), 10-hydroxystearic acid (10-HSA) or 14-hydroxyeicosanoic acid (14-HEA).

Use may be made, as shorter $C_2$-$C_{10}$ acids $R_2'CO_2H$, of acetic, propanoic, butyric, pentanoic (valeric), hexanoic (caproic), heptanoic, octanoic, nonanoic or decanoic acid. Preferably, these optional acids are $C_2$-$C_8$ acids.

The fatty amide according to the invention preferably has a number-average molecular weight Mn measured by GPC in THE as polystyrene equivalents (calibration by polystyrene standards) which for the fatty amide represented by A) according to formula (I) varies for:

n=2 (a diamide) from 800 to 4000, preferably from 1000 to 3800, n=3 (a triamide) from 1000 to 6000, preferably from 2000 to 5500.

The diamide represented by B) according to formula (II) preferably has the same range of number-average molecular weight Mn measured by GPC in THE as polystyrene equivalents (calibration by polystyrene standards) as the diamide represented by A): from 800 to 4000, preferably from 1000 to 3800.

According to a specific option of said fatty amide it is a diamide represented by B) according to formula (II).

According to a preferred option, said oligomer chain segment R1 (according to formula (I) of option A)) is a polyether chain segment.

According to a more particularly preferred option, said oligomer chain segment R1 is a polyoxypropylene chain segment.

Said oligomer chain segment R1 can have a number-average molecular weight Mn ranging from 400 to 2000, preferably from 500 to 1500.

According to a preferred option, said hydroxylated fatty acid $R_2CO_2H$ is selected from 12-hydroxystearic acid (12-HSA), 9- or 10-hydroxystearic acid (9-HSA or 10-HSA), preferably a mixture of 9- and 10-hydroxystearic acids, 14-hydroxyeicosanoic acid (14-HEA) or their mixtures in pairs. The most preferred hydroxylated acid $R_2CO_2H$ is 12-hydroxystearic acid.

Preferably, said monocarboxylic acid $R_2'CO_2H$ is selected from: acetic acid, propionic acid, butyric acid, pentanoic (valeric) acid, hexanoic (caproic) acid, heptanoic acid or octanoic acid.

According to a particularly preferred option, said amide is a diamide or a triamide with all the R2 residues resulting from hydroxylated fatty acid $R_2CO_2H$. More particularly, said amide is a diamide with an R2 residue resulting from hydroxylated fatty acid $R_2CO_2H$.

According to another specific option of the invention, said amide is a triamide with two R2 residues resulting from hydroxylated fatty acid $R_2CO_2H$ and 1 resulting from non-hydroxylated fatty acid $R_2CO_2H$.

The second subject-matter of the invention relates to a formulation composition of an organic binder, characterized in that it comprises:

a) at least one organic binder and b) at least one fatty amide as defined above according to the invention, in particular as rheological additive.

More particularly, in said binder formulation composition, said binder a) is selected from: polysiloxane resins terminated by blocked silane groups, polyether resins terminated by blocked silane groups, polysulfide resins terminated by blocked silane groups, polyurethane prepolymer resins terminated by isocyanate groups, PVC resins for plastisols, epoxy resins carrying epoxy groups.

Said composition can comprise, in addition to a) and b) and depending on said binder, a plasticizer or a reactive diluent as defined below:

c) a plasticizer for polysiloxane resins, polyurethane prepolymer resins and PVC resins for plastisols or d) a reactive diluent from epoxidized monomers for epoxy resins and optionally e) for two-component systems, a hardener for the epoxy or polyurethane resins.

More particularly, in said composition according to the invention, said fatty amide is used as rheological additive which is a thixotropic agent.

In said composition, said organic binder a) can be selected from a polysiloxane resin, a polyurethane prepolymer resin or a PVC resin for plastisols and said plasticizer can be selected from: phthalates, adipates, trimellitates, sebacates, benzoates, citrates, phosphates, epoxides, polyesters, alkylsulfonate esters and non-phthalate substitutes for phthalates.

According to a specific option, said composition is a transparent or non-transparent mastic formulation composition. According to a more specific option, it is a transparent mastic formulation composition.

Another subject-matter of the invention covers the use of at least one fatty amide as defined above according to the invention where said amide is used as rheology additive.

In said use, said rheology additive can be used as thixotropic agent.

More particularly, said use can be in coating, adhesive, PVC plastisol or mastic compositions, preferably PVC plastisol compositions and mastic compositions.

Another specific use is in PVC plastisol compositions.

Another specific use is in mastic compositions which can be crosslinked by moisture based on polysiloxane resins terminated by blocked silane groups, polyether resins terminated by blocked silane groups, polysulfide resins terminated by blocked silane groups, in particular silanes blocked by alkoxy groups, or polyurethane prepolymer resins terminated by isocyanate groups.

Another specific use is in mastic compositions which can be crosslinked by moisture, which mastics are or are not transparent.

Finally, the invention covers a final product which can be a coating, in particular PVC plastisol coating, or an adhesive seal or a mastic seal, which results from the use of at least one fatty amide as defined above according to the invention, as rheology additive and in particular as thixotropic agent.

The following examples of the experimental part below are presented by way of illustration of the invention and of its performance qualities and do not in any way limit its scope.

EXPERIMENTAL PART

1) Starting Materials Used and Codes

See Table 1 below

TABLE 1

Table summarizing the starting materials used in synthesis and in formulations

| Product used | Chemical name | Function | Supplier |
|---|---|---|---|
| 12HSA | 12-Hydroxystearic acid | Hydroxylated fatty acid | Jayant Agro |
| Stearine | Stearic acid | Non-hydroxylated fatty acid | Sogis |
| Jeffamine ® T-3000 Polyetheramine | Jeffamine ® T-3000 polyetheramine | Polyoxypropylene triamine (primary) with overall ~50 oxypropylene (OP) units | Huntsman |
| Jeffamine ® D-2000 Polyetheramine | Jeffamine ® D-2000 polyetheramine | Polyoxypropylene diamine (primary) with ~33 OP units | Huntsman |
| HCO (as flakes) | Hydrogenated castor oil | Reference rheology additive | Gokul Agro |
| Crayvallac ® Antisettle CVP (micronized powder) | Hydrogenated castor oil | Reference rheology additive | Arkema |
| Standard fatty diamide | 12HSA-HMDA-12HSA | Reference diamide rheology additive for comparison | / |
| MS Polymer ® S203H | Silylated polyether | Applicative formulation resin | Kaneka |
| Jayflex ® DIUP | Diisoundecyl phthalate | Plasticizer | BASF |

For reasons of clarity, the following abbreviations will be used:

12HSA: 12-Hydroxystearic acid
SA: Stearic acid
HMDA: Hexamethylenediamine
D2000: Jeffamine® D-2000 polyetheramine
T3000: Jeffamine® T-3000 polyetheramine

2) Examples

Example A According to the Invention—T3000-12HSA$_3$ 305.9 g of Jeffamine® T-3000 (0.099 mol, 1 eq) and 94.1 g of 12-hydroxystearic acid (0.297 mol, 3 eq) are added to a 1 litre round-bottomed flask equipped with a thermometer, a Dean and Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 6, the reaction is halted. The reaction mixture is cooled to 140° C. and is discharged into a silicone mould. Once cooled to ambient temperature, the product is converted into flakes.

Example B According to the Invention—12HSA-D2000-12HSA 304.4 g of Jeffamine® D-2000 (0.15 mol, 1 eq) and 95.6 g of 12-hydroxystearic acid (0.3 mol, 2 eq) are added to a 1 litre round-bottomed flask equipped with a thermometer, a Dean and Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 6, the reaction is halted. The reaction mixture is cooled to 140° C. and is discharged into a silicone mould. Once cooled to ambient temperature, the product is converted into flakes.

Example C Comparative—T3000-SA$_3$ 313.6 g of Jeffamine® T-3000 (0.10 mol, 1 eq) and 86.4 g of stearic acid (0.3 mol, 3 eq) are added to a 1 litre round-bottomed flask equipped with a thermometer, a Dean and Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 6, the reaction is halted. The reaction mixture is cooled to 140° C. and is discharged into a silicone mould.

Example D Comparative—SA-D2000-SA 312.2 g of Jeffamine® D-2000 (0.15 mol, 1 eq) and 87.8 g of stearic acid (0.3 mol, 2 eq) are added to a 1 litre round-bottomed flask equipped with a thermometer, a Dean and Stark apparatus, a condenser and a stirrer. The mixture is heated to 180° C. under an inert atmosphere. The water removed accumulates in the Dean and Stark apparatus from 150° C. The reaction is monitored by the acid number and the amine number. When the acid and amine numbers are respectively less than 6, the reaction is halted. The reaction mixture is cooled to 140° C. and is discharged into a silicone mould.

3) Study of the Gelling Power of the Organogelators

In this comparative example, the ability of the rheology additives to form a gel in a simplified formulation containing solely a conventional plasticizer (Jayflex® DIUP) used in PVC plastisol formulations will be studied.

The formulations are prepared using a laboratory "planetary" mixer (Molteni® EMD 1 type) provided with a dispersing disc and a scraper which makes it possible to mix high-viscosity products but also powders in non-fluid systems. It is equipped with a vacuum pump which makes it possible to prevent the ingress of moisture during the dispersing. The temperature within the Molteni® EMD 1 is recorded by a probe attached to the scraper and can be regulated by virtue of a bath.

TABLE 2

Composition of the simplified formulations

| Formulation | Component | % wt | Function |
|---|---|---|---|
| F1 | Jayflex ® DIUP | 95 | Plasticizer |
| | T3000-12HSA$_3$ | 5 | Rheology additive |
| F2 | Jayflex ® DIUP | 95 | Plasticizer |
| | 12HSA-D2000-12HSA | 5 | Rheology additive |
| F3 | Jayflex ® DIUP | 95 | Plasticizer |
| | T3000-SA$_3$ | 5 | Rheology additive |
| F4 | Jayflex ® DIUP | 95 | Plasticizer |
| | SA-D2000-SA | 5 | Rheology additive |

TABLE 2-continued

Composition of the simplified formulations

| Formulation | Component | % wt | Function |
|---|---|---|---|
| F5 | Jayflex ® DIUP | 95 | Plasticizer |
| | 12HSA-HMDA-12HSA | 5 | Rheology additive |
| F6 | Jayflex ® DIUP | 95 | Plasticizer |
| | HCO | 5 | Rheology additive |
| F7 | Jayflex ® DIUP | 95 | Plasticizer |
| | Crayvallac ® | 5 | Rheology additive |
| | Antisettle CVP | | |

The rheology additive is introduced into the plasticizer and the mixture is brought to the incorporation temperature (cf. Table 3) and dispersed for 5 minutes. At the end of the dispersing, the mixture is cooled to ambient temperature and the behaviour of the gel is studied visually.

TABLE 3

Behaviour and appearance of the gel as a function of the incorporation temperature

| Formulation | Temperature | Behaviour of the gel | Appearance |
|---|---|---|---|
| F1 | 60° C.** | Strong gel | Transparent |
| | 80° C.** | Strong gel | Transparent |
| F2 | 60° C.** | Strong gel | Transparent |
| | 80° C.** | Strong gel | Transparent |
| F3 | 60° C.** | Liquid | Transparent |
| | 80° C.** | Liquid | Transparent |
| F4 | 60° C.** | Liquid | Transparent |
| | 80° C.** | Liquid | Transparent |
| F5 | 60° C.* | Weak gel | Opaque |
| | 80° C.* | Weak gel | Opaque |
| | 100° C.** | Weak gel | Opaque |
| F6 | 60° C.* | Weak gel (presence of grains) | Opaque |
| | 80° C.** | Weak gel | Opaque |
| F7 | 60° C.* | Strong gel | Opaque |
| | 80° C.** | Weak gel (slight syneresis) | Opaque |

*partial dissolution;
**complete dissolution

The results of the gel tests show that the products according to the invention (T3000-12HSA$_3$, 12HSA-D2000-12HSA) form gels, while the comparative products are in the liquid form. Thus, the compound T3000-SA$_3$ described in particular in patent EP 1 514 912 A2 does not make it possible to obtain the gel (cf Formulation F3), which strongly indicates that the presence of the hydroxyl group is essential to the formation of the supramolecular assemblage and of the 3D network of fibres.

The behaviour of the organogelator agents can also be influenced by the initial structure of the diamine used. Thus, on comparing the organogelator described in WO 2014/053774A1 (12HSA-HMDA-12HSA) with the compound 12HSA-D2000-12HSA according to the invention, a significant difference in gel strength may be observed. In particular, if the aliphatic amine is replaced with a polyether amine, the gelling power increases, making it possible, in addition, to obtain a transparent gel. It should be noted that, in order to be completely dissolved, the compound 12HSA-HMDA-12HSA (cf Formulation F5) requires greater temperatures than the products according to the invention.

Furthermore, the performance qualities of the gels can be linked to the physical nature of the rheology additive. Consequently, for formulations F6 and F7 to begin with at a constant temperature (60° C.) of incorporation of the rheology additive, a difference in gel strength is observed. Namely, if the additive is in the form of flakes (cf Formulation F6), the gel strength will decrease, which might well be explained by an incomplete incorporation of the product in the formulation due to the lack of solubility. Furthermore, grains could be observed, which might corroborate this hypothesis.

Also, it may be observed that, if the additive in the powder form is incorporated at a higher temperature (80° C. in F7) than its optimum temperature (60° C. in F7), the gel strength will decrease, which shows in addition a sensitivity to the temperature due probably to the complete dissolution of the product. It is thus important, in the case of the standard products, to indeed observe a temperature window in which organogelator is effective.

As regards formulations F1 and F2 based on the products according to the invention, the formation of a strong gel, irrespective of the incorporation temperature, may be observed. It should be mentioned that, at the temperatures studied, the rheology additive is completely dissolved. Furthermore, the formulations exhibit a completely transparent appearance.

4) Evaluation of the Rheological Performance Qualities in a Simplified Hybrid Mastic Formulation In this comparative example, the rheological performance qualities of the additives of a simplified hybrid mastic formulation will be illustrated.

TABLE 4

Composition of the simplified formulations

| Formulation | Component | % wt | Function |
|---|---|---|---|
| F8 | Jayflex ® DIUP | 47.5 | Plasticizer |
| | MS-Polymer ® S 203 H | 47.5 | Resin |
| | T3000-12HSA$_3$ | 5 | Rheology additive |
| F9 | Jayflex ® DIUP | 47.5 | Plasticizer |
| | MS-Polymer ® S 203 H | 47.5 | Resin |
| | Crayvallac Antisettle CVP | 5 | Rheology additive |
| F10 | Jayflex ® DIUP | 47.5 | Plasticizer |
| | MS-Polymer ® S 203 H | 47.5 | Resin |
| | 12HSA-D2000-12HSA | 5 | Rheology additive |
| F11 | Jayflex ® DIUP | 47.5 | Plasticizer |
| | MS-Polymer ® S 203 H | 47.5 | Resin |
| | 12HSA-HMDA-12HSA | 5 | Rheology additive |

In order to do this, the formulations are prepared using the same Molteni® EMD1 mixer. The resin and the plasticizer are added and homogenized in a first stage and in the proportions shown. The additive is weighed out and subsequently added during the second stage. Thus, the reaction mixture, which is kept under vacuum during the mixing phases, is brought to 80° C. for 5 minutes. At the end of this phase, the mixture is cooled to 25° C. and discharged.

TABLE 5

Rheological performance qualities

| Formulation | Viscosity at 0.1 s$^{-1}$ (Pa · s) | Viscosity at 100 s$^{-1}$ (Pa · s) | Thixotropic index | Yield point (Pa) | Appearance |
|---|---|---|---|---|---|
| F8 | 995 | 4.57 | 218 | 86.0 | Transparent |
| F9 | 296 | 6.06 | 49 | 4.4 | Opaque |

TABLE 5-continued

| | Viscosity at 0.1 s$^{-1}$ (Pa · s) | Viscosity at 100 s$^{-1}$ (Pa · s) | Thixotropic index | Yield point (Pa) | Appearance |
|---|---|---|---|---|---|
| Formulation | | | | | |
| F10 | 374 | 3.40 | 110 | 32.0 | Transparent |
| F11 | 47 | 2.21 | 21 | 3.1 | Opaque |

Rheological performance qualities

The triamide rheology additive T3000-12HSA$_3$ according to the invention proves to be much more effective in terms of rheological performance qualities (cf Formulation F8), compared with the standard powder additive Crayvallac® Antisettle CVP (cf Formulation F9). With regard to the diamide product 12HSA-D2000-12HSA, it also exhibits rheological performance qualities (cf Formulation F10) which are superior to that using the compound in the powder form 12HSA-HMDA-12HSA (cf Formulation F11).

Furthermore, the products according to the invention do not need a specific processing process to develop the rheology, as is the case for conventional additives in the form of powders based on hydrogenated castor oil derivatives.

Furthermore, as the products according to the invention are in the form of flakes, problems encountered with the use of powders (handling, toxicity, and the like) are thus eliminated. It should also be noted that these products make it possible to obtain MS mastic formulations which are completely transparent.

The invention claimed is:

1. A polyfunctional fatty amide which is a diamide or a triamide or a mixture thereof, wherein said polyfunctional fatty amide is represented by:

A) formula (I):

$$[(R2'—OCNH-R1-X)n1—R—(X—R1—NHCO—R2)n—n1] \quad (I)$$

with n being 2 or 3, n$_1$ being equal to 0 or 1,

R1 being a bivalent oligomer chain segment chosen from alkoxylated polyester and polyether, R being a C$_3$-C$_{10}$ bivalent or trivalent alkylene, X being O, NH or N(R3), R2 being a hydroxylated or non-hydroxylated C12-C52 hydrocarbon chain of a monocarboxylic fatty acid, wherein said R2 are identical or different when n-n1 is >1, wherein at least one R2 is a hydroxylated C$_{12}$-C$_{52}$ hydrocarbon chain with a non-terminal hydroxyl group, and wherein the monocarboxylic fatty acid excludes any polyester or oligoester derived from the self-polycondensation of a hydroxylated fatty acid, R2' being a C$_2$ to C$_{10}$ hydrocarbon chain of a monocarboxylic acid, and R3 being a C1-C2 alkyl substituent, or by B) formula (II), wherein said polyfunctional fatty amide is a diamide:

$$R2CONH-R'—O—[CH2—CH(R4)—O]_x—CH2—CH(R4)—NHCOR2' \quad (II)$$

with R' being —CH(CH3)—CH2—

R2 and R2' being defined as in said formula (I), and each R4 being independently H or methyl wherein the value of x is such that a number-average molecular weight Mn of the polyfunctional fatty amide, measured by gel permeation chromatography in tetrahydrofuran as polystyrene equivalents, is from 800 to 4000 when n in formula (I) is 2 and from 1,000 to 6,000 when n in formula (I) is 3, and wherein said polyfunctional fatty amide has a melting temperature ranging from 10°C. to 110°C., as measured after two passes on a differential scanning calorimetry ("DSC") having a temperature ramp rate of 10°C./min.

2. The polyfunctional fatty amide according to claim 1 wherein said bivalent oligomer chain segment R1 is a polyether chain segment.

3. The polyfunctional fatty amide according to claim 1 wherein said bivalent oligomer chain segment R1 is a polyoxypropylene chain segment.

4. The polyfunctional fatty amide according to claim 1 wherein R1 has a number-average molecular weight (Mn) ranging from 400 to 2000.

5. The polyfunctional fatty amide according to claim 1 wherein said monocarboxylic fatty acid is a hydroxylated fatty acid selected from 12-hydroxystearic acid (12-HSA), 9-hydroxystearic acid (9-HSA), 10-hydroxystearic acid (10-HSA), a mixture of 9- and 10-hydroxystearic acids, and 14-hydroxyeicosanoic acid (14-HEA).

6. The polyfunctional fatty amide according to claim 1 wherein said monocarboxylic fatty acid is 12-hydroxystearic acid.

7. The polyfunctional fatty amide according to claim 1 wherein R2' is a C$_2$ to C$_{10}$ hydrocarbon chain of a monocarboxylic acid selected from the group consisting of: acetic acid, propionic acid, butyric acid, pentanoic (valeric) acid, hexanoic (caproic) acid, heptanoic acid, and octanoic acid.

8. The polyfunctional fatty amide according to claim 1 wherein said polyfunctional fatty amide is a diamide according to A) or B) or a triamide according to A) with all R2 groups being a hydroxylated C$_{12}$-C$_{52}$ hydrocarbon chain of a monocarboxylic fatty acid.

9. The polyfunctional fatty amide according to claim 1 wherein said polyfunctional fatty amide is a diamide according to A) or B) with one R2 group being a hydroxylated C$_{12}$-C$_{52}$ hydrocarbon chain of a monocarboxylic fatty acid.

10. The polyfunctional fatty amide according to claim 1 wherein said polyfunctional fatty amide is a triamide according to A) with two R2 groups being a hydroxylated C$_{12}$-C$_{52}$ hydrocarbon chain of a monocarboxylic fatty acid and one R2 group being a non-hydroxylated C$_{12}$-C$_{52}$ hydrocarbon chain of a monocarboxylic fatty acid.

11. The polyfunctional fatty amide according to claim 1 wherein the polyfunctional fatty amide is a diamide represented by A) according to formula (I).

12. The polyfunctional fatty amide according to claim 1 wherein the polyfunctional fatty amide is a diamide represented by B) according to formula (II).

13. A formulation composition of an organic binder comprising:

a) at least one organic binder, and b) at least one polyfunctional fatty amide as defined according to claim 1.

14. The composition according to claim 13, wherein said at least one organic binder a) is selected from the group consisting of: polysiloxane resins terminated by blocked silane groups, polyether resins terminated by blocked silane groups, polysulfide resins terminated by blocked silane groups, polyurethane prepolymer resins terminated by isocyanate groups, polyvinyl chloride (PVC) plastisols, and epoxy resins carrying epoxy groups.

15. The composition according to claim 13 further comprising a plasticizer or a reactive diluent as defined below:

c) a plasticizer selected from the group consisting of phthalates, adipates, trimellitates, sebacates, benzoates, citrates, phosphates, epoxides, polyesters, alkylsulfonate esters and non-phthalate substitutes for phthalates, or d) a reactive diluent selected from epoxidized monomers, and e) optionally, a hardener for the epoxy or polyurethane resins.

16. The composition according to claim 13 wherein said polyfunctional fatty amide is a thixotropic agent.

17. The composition according to claim 15 wherein said organic binder a) is a polysiloxane resin, a polyurethane prepolymer resin or a PVC plastisol.

18. The composition according to claim 17, wherein the composition is a transparent or non-transparent mastic formulation composition.

* * * * *